US010603082B2

(12) United States Patent
Lish

(10) Patent No.: US 10,603,082 B2
(45) Date of Patent: Mar. 31, 2020

(54) BONE ANCHOR

(71) Applicant: NuVasive, Inc., San Diego, CA (US)

(72) Inventor: Scott Lish, Oceanside, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 16/051,477

(22) Filed: Jul. 31, 2018

(65) Prior Publication Data

US 2019/0021769 A1      Jan. 24, 2019

Related U.S. Application Data

(63) Continuation of application No. 15/365,383, filed on Nov. 30, 2016, now Pat. No. 10,034,691.

(60) Provisional application No. 62/262,530, filed on Dec. 3, 2015.

(51) Int. Cl.
*A61B 17/70*     (2006.01)
*A61B 17/86*     (2006.01)

(52) U.S. Cl.
CPC ...... *A61B 17/7035* (2013.01); *A61B 17/7002* (2013.01); *A61B 17/7034* (2013.01); *A61B 17/7037* (2013.01); *A61B 17/8615* (2013.01)

(58) Field of Classification Search
CPC ............ A61B 17/7035; A61B 17/7002; A61B 17/7034; A61B 17/7037; A61B 17/8615
USPC .......... 606/266, 269, 270; 403/362; 411/393
See application file for complete search history.

(56) References Cited

U.S. PATENT DOCUMENTS

| | | |
|---|---|---|
| 5,891,145 A | 4/1999 | Morrison et al. |
| 5,989,254 A | 11/1999 | Katz |
| 6,113,601 A | 9/2000 | Tatar |
| 6,187,005 B1 | 2/2001 | Brace et al. |
| 6,719,759 B2 | 4/2004 | Wagner et al. |
| 6,736,820 B2 | 5/2004 | Biedermann et al. |
| 6,755,830 B2 | 6/2004 | Minfelde et al. |
| 6,837,889 B2 | 1/2005 | Shluzas |
| 6,974,460 B2 | 12/2005 | Carbone et al. |
| 7,163,539 B2 | 1/2007 | Abdelgany et al. |
| 7,204,853 B2 | 4/2007 | Gordon et al. |
| 7,223,268 B2 | 5/2007 | Biedermann |
| 7,250,052 B2 | 7/2007 | Landry et al. |
| 7,264,621 B2 | 9/2007 | Coates et al. |
| 7,377,923 B2 | 5/2008 | Purcell et al. |
| 7,530,992 B2 | 5/2009 | Biedermann et al. |
| 7,635,380 B2 | 12/2009 | Zucherman et al. |
| 7,678,137 B2 | 3/2010 | Butler et al. |
| 7,727,261 B2 | 6/2010 | Barker et al. |
| 7,785,354 B2 | 8/2010 | Biedermann et al. |
| 7,819,902 B2 | 10/2010 | Abdelgany et al. |
| 7,862,588 B2 | 1/2011 | Abdou |
| 7,947,065 B2 | 5/2011 | Hammill et al. |

(Continued)

FOREIGN PATENT DOCUMENTS

DE      19950075     4/2001

*Primary Examiner* — Pedro Philogene
*Assistant Examiner* — David C Comstock

(57) ABSTRACT

A bone anchor having a rod housing including a base that has an internal groove oriented at an angle oblique to the longitudinal axis of the base, a capture ring situated within the groove and oriented at an angle oblique to the longitudinal axis, and a bone fastener extending into the rod housing and including a fastener head situated within the base and having a surface that mates with the capture surface of the capture ring to maintain a connection between the bone fastener and the rod housing.

20 Claims, 2 Drawing Sheets

(56) References Cited

U.S. PATENT DOCUMENTS

| | | |
|---|---|---|
| 7,955,358 B2 | 6/2011 | Albert |
| 7,955,364 B2 | 6/2011 | Ziolo et al. |
| 8,002,806 B2 | 8/2011 | Justis |
| 8,012,177 B2 | 9/2011 | Jackson |
| 8,021,397 B2 | 9/2011 | Farris et al. |
| 8,100,946 B2 | 1/2012 | Strausbaugh et al. |
| 8,337,530 B2 | 12/2012 | Hestad et al. |
| 9,131,962 B2 | 9/2015 | Cahill et al. |
| 9,539,012 B2 | 1/2017 | Landry et al. |
| 10,034,691 B1 * | 7/2018 | Lish .................. A61B 17/7035 |
| 2003/0100896 A1 | 5/2003 | Biedermann et al. |
| 2004/0153077 A1 | 8/2004 | Biedermann et al. |
| 2005/0080415 A1 | 4/2005 | Keyer et al. |
| 2005/0154391 A1 | 7/2005 | Doherty et al. |
| 2005/0154393 A1 | 7/2005 | Doherty et al. |
| 2006/0084978 A1 | 4/2006 | Mokhtar |
| 2006/0084979 A1 | 4/2006 | Jackson |
| 2007/0213720 A1 | 9/2007 | Gordon et al. |
| 2007/0265621 A1 | 11/2007 | Mathis et al. |
| 2008/0039844 A1 | 2/2008 | Jackson |
| 2008/0077143 A1 | 3/2008 | Shluzas |
| 2008/0132953 A1 | 6/2008 | Carbone et al. |
| 2008/0161859 A1 | 7/2008 | Nilsson |
| 2008/0177260 A1 | 7/2008 | McKinley et al. |
| 2008/0208256 A1 | 8/2008 | Thramann |
| 2009/0005815 A1 | 1/2009 | Ely |
| 2009/0082812 A1 | 3/2009 | Lewis |
| 2009/0198280 A1 | 8/2009 | Spratt et al. |
| 2010/0145394 A1 | 6/2010 | Harvey et al. |
| 2010/0160977 A1 | 6/2010 | Gephart et al. |
| 2010/0204735 A1 | 8/2010 | Gephart et al. |
| 2011/0087288 A1 | 4/2011 | Stevenson et al. |
| 2011/0125195 A1 | 5/2011 | Biedermann et al. |
| 2011/0178559 A1 | 7/2011 | Barry |

* cited by examiner

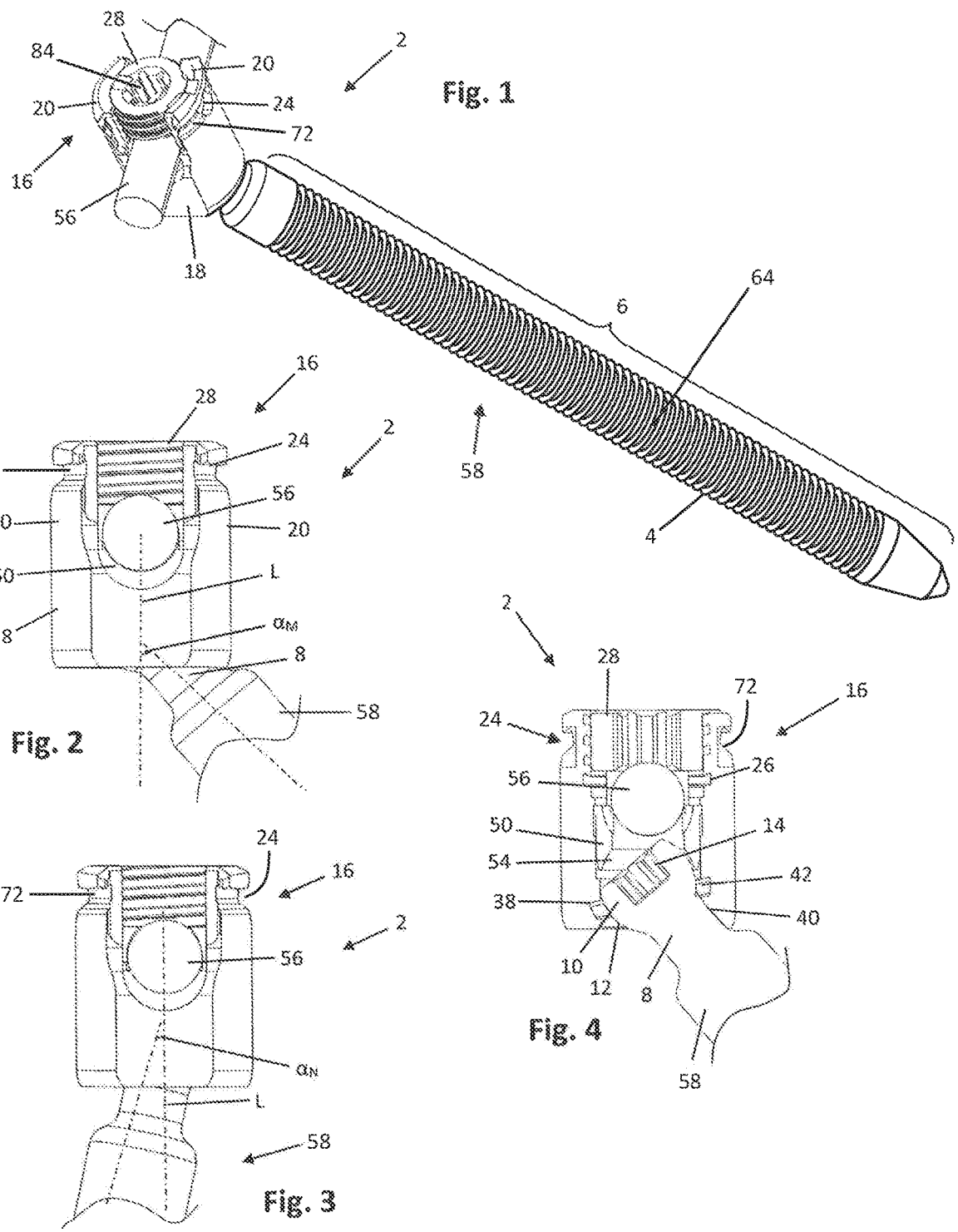

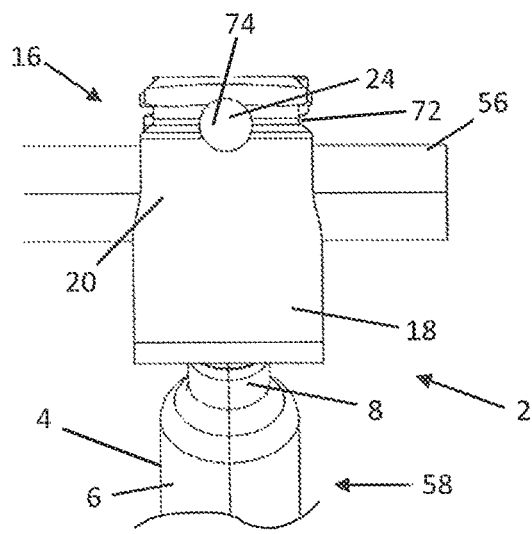
Fig. 5
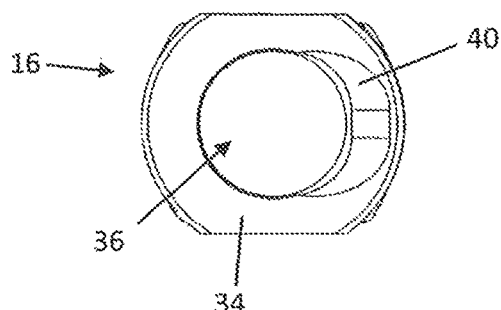
Fig. 6
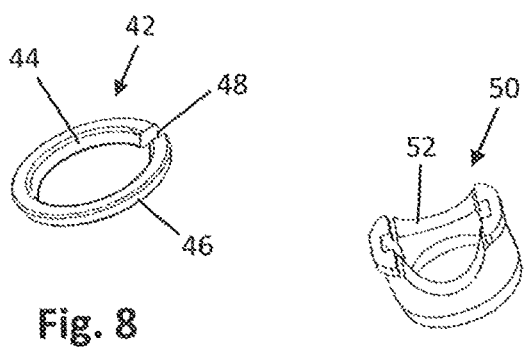
Fig. 8
Fig. 9
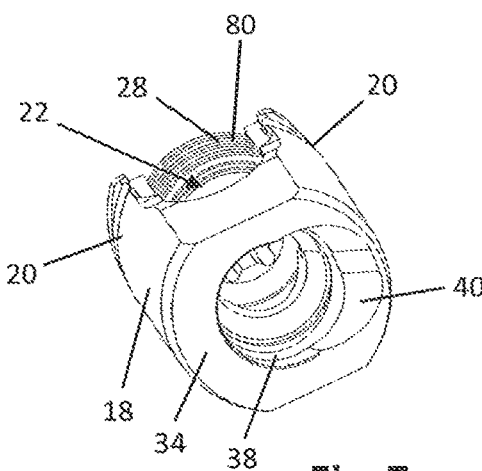
Fig. 7
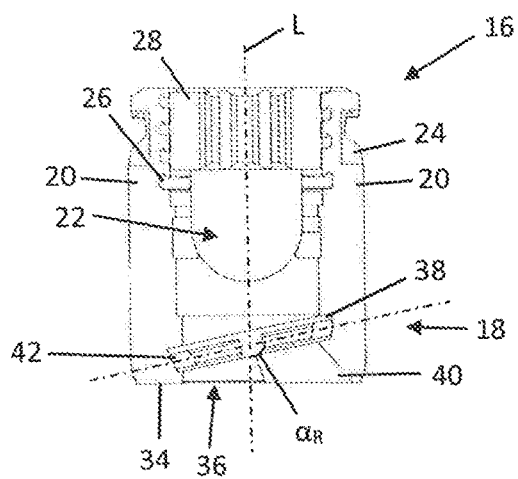
Fig. 10
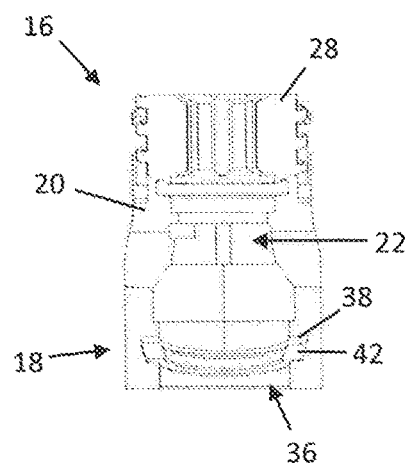
Fig. 11

BONE ANCHOR

CROSS-REFERENCE TO RELATED APPLICATIONS

This application claims the benefit of U.S. Provisional Application Ser. No. 62/262,530, filed 3 Dec. 2015, which is incorporated herein by reference in its entirety.

FIELD

The present disclosure relates generally to medical devices, more specifically to the field of spinal surgery and spinal fixation devices. Such devices as well as systems and methods for use therewith are described.

BACKGROUND

The spine is critical in human physiology for mobility, support, and balance. The spine protects the nerves of the spinal cord, which convey commands from the brain to the rest of the body, and convey sensory information from the nerves below the neck to the brain. Even minor spinal injuries can be debilitating to the patient, and major spinal injuries can be catastrophic. The loss of the ability to bear weight or permit flexibility can immobilize the patient. Even in less severe cases, small irregularities in the spine can put pressure on the nerves connected to the spinal cord, causing devastating pain and loss of coordination.

Surgical procedures on the spine often include the immobilization of two or more vertebra. Immobilizing the vertebrae may be accomplished in many ways (e.g. fixation plates and pedicle screw systems). One of the most common methods for achieving the desired immobilization is through the application of bone anchors (most often introduced into the pedicles associated with the respective vertebra to be fixed) that are then connected by rigid rods locked to each pedicle screw. These pedicle screw systems are very effective. Pedicle screws generally include an anchor component and a rod-housing component (or "tulip") that is often coupled to the anchor component in a manner that permits angular adjustability of the tulip relative to the anchor component in one or more planes. Once the pedicle screws are implanted in the desired positions a spinal rod is seated in each tulip and locked in position. The angular adjustability of the tulips is also locked, either through the locking of the rod, or independently thereof, to thus fix the connected vertebrae relative to each other. Pedicle screw configurations which allow increased angulation of the housing component in one direction are useful in certain situations where an increased pivot angle is needed (e.g. where there is an acute angle between the anchor component and rod trajectories, such as occurs, for example, with S2-Alar screws). However, configurations that permit the increased angulation also tend to reduce the strength of the connection between the anchor component and rod-housing component. Therefore a need exists for new and improved anchors with increased angulation housings but without the reduction in connection strength suffered in current solutions.

SUMMARY

The needs described above, as well as others, are addressed by embodiments of a bone anchor described in this disclosure (although it is to be understood that not all needs described above will necessarily be addressed by any one embodiment).

A bone anchor with increased range of angulation is provided having a rod-housing connected to a bone fastener. The bone fastener includes a head and a bone engagement feature (such as screw threads) that serve as a means to fasten the anchor to a bone structure (e.g., a pedicle). The rod housing connects the bone anchor to a spinal fixation rod that may in turn be connected to one or more additional bone anchors on other bone structures. The rod housing has a longitudinal axis that is adjustable through a range of angles (including 0°) to the longitudinal axis of the bone fastener. The degree of angulation achievable may vary depending on the direction of angulation. This may be facilitated in part by the use of a capture ring with an oblique orientation relative to the longitudinal axis that contains a head section of the bone fastener on this distal side.

A general embodiment of the bone anchor comprises a rod housing including a base, a pair of upright arms extending from the base to an upper proximal end, and a longitudinal axis extending though a distal opening in the base and a proximal opening in the upper proximal end, the pair of upright arms separated by a rod channel, and the base including an internal groove oriented at an angle oblique to the longitudinal axis; a capture ring situated within the groove and oriented at an angle oblique to the longitudinal axis, the capture ring having a capture surface; and a bone fastener extending through the distal opening in the rod housing and including a fastener head and a bone engagement feature, the head situated within the base and having a surface that mates with the capture surface of the capture ring to maintain a connection between the bone fastener and the rod housing.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF THE DRAWINGS

FIG. 1. A perspective view of an embodiment of the bone anchor.

FIG. 2. A side view of the rod housing shown in FIG. 1. The maximum deflection angle ($\alpha_M$) of the bone fastener relative to the longitudinal axis of the rod housing (L) is shown.

FIG. 3. A side view of the rod housing shown in FIG. 1. The nominal deflection angle ($\alpha_N$) of the bone fastener relative to the longitudinal axis of the rod housing (L) is shown.

FIG. 4. A cross-sectional view of the embodiment of the bone anchor shown in FIG. 1.

FIG. 5. A front view of the rod housing shown in FIG. 1.

FIG. 6. A top view of the rod housing shown in FIG. 1.

FIG. 7. A perspective view of the rod housing shown in FIG. 1, without the bone fastener shown, revealing detail of the recess on the inner wall of the rod housing.

FIG. 8. A perspective view of an embodiment of the capture ring.

FIG. 9. A perspective view of an embodiment of the load ring.

FIG. 10. A side cross-sectional view of the embodiment of the rod housing shown in FIG. 1, with the bone fastener and rod omitted.

FIG. 11. A front cross-sectional view of the embodiment of the rod housing shown in FIG. 1, with the bone fastener and rod omitted.

DETAILED DESCRIPTION

Illustrative embodiments of a spinal fixation anchor are described below. In the interest of clarity, not all features of an actual implementation are described in this specification. It will of course be appreciated that in the development of any such actual embodiment, numerous implementation-specific decisions must be made to achieve the developers' specific goals, such as a compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal anchor assembly disclosed herein boasts a variety of inventive features and components that warrant patent protection, both individually and in combination.

A bone anchor 2 is provided having a rod housing 16 connected to a bone fastener 58. The bone fastener 58 includes a shank 4 with a bone engagement feature 64 (such as screw threads) that serve as a means to fasten the anchor 2 to a bone structure (e.g., a pedicle). The rod housing 16 connects the bone anchor 2 to a spinal fixation rod 58 that may in turn be connected to one or more additional bone anchors 2 on other bone structures. The rod housing 16 has a longitudinal axis that is adjustable through a range of angles (including 0°) to the longitudinal axis L of the bone fastener 58. The degree of angulation achievable may vary depending on the direction of angulation. This may be facilitated in part by the use of a capture ring 42 with an oblique orientation relative to the longitudinal axis L that constrains the translocation of a head section 10 of the bone fastener 58 on the distal direction.

The rod housing 16 comprises a base 18, a pair of upright arms 20 extending from the base 18 to an upper proximal end, and a longitudinal axis L extending though a distal opening 36 in the base 18 and a proximal opening 104 in the upper proximal end. The rod channel 22 runs between the pair of upright arms 20. When in use, the rod channel 22 contains the spinal fixation rod 58; therefore the rod channel 22 may be dimensioned to accommodate a spinal fixation rod 58 (the rod may be of any suitable dimensions known in the art). The rod channel 22 may take a variety of shapes, and in some embodiments has a U-shaped profile that is complementary to a cylindrical rod 58 on the proximal side (i.e., the bottom portion of the "U"). Some embodiments of the rod channel 22 are open at the proximal end in order to allow the rod 58 to be emplaced from the proximal direction, although other configurations are possible. As shown in FIGS. 1-3 a locking element 68 (such as a locking cap 28 as illustrated) may be placed proximal to the rod channel 22, to constrain the rod 58 from proximal displacement.

The upright arms 20 extend on either side of the rod channel 22. The arms 20 may include attachment features 24 for coupling to various tools useful during implantation of the bone anchor 2 and associated fixation construct (e.g., inserters, reducers, and other such tools as are known in the art). In the specific embodiment shown in FIGS. 1-5 and 10-11, the attachment features 24 comprise a circumferential slot 72 on both arms 22 just below the proximal end of each arm 22, and an indentation 74 that meets the distal side of the circumferential slot 72. Together the circumferential slot 72 and the indentation 74 allow a tool to connect to the bone anchor 2 in such a way that the tool will neither translate longitudinally nor rotate circumferentially while attached. Other configurations of course may be used.

The upright arms 20 may comprise a locking element engagement feature 76 that cooperates with a locking element 68 to capture and lock a rod 58 in the rod channel 22. In a certain embodiment of the bone anchor 2, the upright arms 20 comprise helical guide features 78 that cooperate with complementary helical guide features 80 of a locking cap 28. Alternatively, the upright arms 20 could have internal helical flanges 82 that cooperate with the threads of a locking cap 28. The locking element engagement feature 76 is configured such that the locking element 68 functions to exert force with a distal vector on the rod 58, providing a means to reduce the rod 58 and seat it in the channel. In the illustrated embodiment the locking cap 28 has a driver engagement feature 14 to allow a driving tool to engage and to drive the cap. In the particular illustrated embodiment the driver engagement feature 14 is a hexalobular internal feature.

The base 18 functions to mate with one end of the bone fastener 58 and comprises an internal groove 38 oriented at an angle oblique to the longitudinal axis L. As will become apparent in the discussion below, the obliqueness of the internal groove 38 allows the bone fastener 58 to deflect over a wider angular range than would otherwise be possible. In some embodiments of the base 18 the distal opening 36 is defined by an internal wall portion 92 of the base 18. The geometry of the base can be varied to allow more or less deflection of the bone fastener 58 relative to the base's 18 longitudinal axis. One example of such useful geometry is shown in FIG. 7. It takes the form of a recess 40 that is formed in a bottom surface of the base. The recess 40 is formed on one side of the base, as in FIG. 7, to align with a high side of the angled capture ring. A recess 40 on one side has the advantage of allowing an increase in deflection in a specific direction while only minimally detracting from the strength of the rod housing 16. In some embodiments the recess 40 may be scalloped to complement a shank 4 or neck 8 of the bone fastener 58 that may be narrower in diameter than the distal opening 36 itself. The recess 40 will generally form an angle with the longitudinal axis L that is at least as great as the angle of the internal groove 38. In some embodiments the recess 40 forms an angle with the longitudinal axis L that is greater than the angle of the internal groove 38. The greater the angle formed between the longitudinal axis L and the recess 40, the more freedom to deflect the bone fastener 58 will have. Absent such a recess 40, the maximum angle formed between the longitudinal axis L and the bone fastener 58 ($\alpha_M$) will be limited.

The housing 16 includes an internal ring groove 38 oriented at an angle ($\alpha_R$) oblique to the longitudinal axis L. The ring groove 38 is oriented at an angle $\alpha_R$ relative to the longitudinal axis L to shift the nominal ($\alpha_N$) and maximum angle ($\alpha_M$) of the shank 4 relative to one side of the housing 16. In the example shown, the angle $\alpha_R$ is approximately 12', the angle $\alpha_M$ is approximately 50°, and the angle $\alpha_N$ is approximately 10'. The surface of the internal ring groove 38 will generally complement the shape of the capture ring 42. For example, in embodiments in which the capture ring 42 has a frusto-spherical external contour 46, the surface of the internal groove 38 will have at least a portion that is complementary to the frusto-spherical external contour 46. As used herein, the prefix "frusto" denotes a frustum of a specified shape and "frustum" means part of a solid (such as a cone or sphere) intersected between two planes that are either parallel or roughly parallel. For example, a frusto-conical solid is a frustum of a cone, and a frusto-spherical solid is a frustum of a sphere.

The capture ring 42 itself sits in the internal groove 38 and serves to prevent displacement of the fastener head 58 from the rod housing 16 in the distal direction. Some embodiments of the capture ring 42 contain the fastener head 58 by virtue of having a minimum diameter that is less than a maximum diameter of the fastener head 58. In the illustrated example in FIG. 4, the fastener head 58 has a uniform diameter around the equator of the frustum of the sphere that is greater than the internal diameter of the capture ring 42. The capture ring 42 may also have an external contour 46 that allows it to articulate relative to the rod housing 16. For example, a capture ring 42 with a frustoconical external contour 46 can rotate around its own center within the groove 38. As another example, a ring with a frusto-spherical external contour 46 can rotate around its own center and deflect relative to the rod housing 16. A specific embodiment of the capture ring 42 has a frusto-spherical outer contour 46 and a frusto-spherical inner contour 44. The capture ring 42 may have additional features to facilitate easy installation. One such feature is a slit 48 through the ring that allows it to be compressed for easy insertion into the groove 38. The slit 48 will generally penetrate entirely through one section of the ring 42.

The bone anchor 2 may further comprise a load ring 50 positioned within the base distal to the rod channel 22 and proximal to the capture ring 42. The load ring 50 is positioned to exert compressing force on the fastener head 10 with a distal vector when the load ring 50 receives compressing force with a distal vector. In an exemplary embodiment of the anchor comprising the load ring 50, the locking element 68 exerts a compressive force with a distal vector on the spinal rod 60 when the locking element 68 is tightened using the helical guides on the upright arms 20, which in turn exerts compressive force with a distal vector on the load-ring 50. The upper (proximal) surface 60 of the load ring 50 may be shaped to prevent it from interfering with the rod 58. In the example shown in FIG. 9, the proximal surface 52 of the load ring 50 has two dips opposite one another to provide space for the rod 58. The load ring 50 in turn exerts compressing force against the head 10 of the bone fastener 58, which locks the bone fastener 58 in a desired orientation. Prior to the exertion of such compressing force by the load ring 50 on the bone fastener head 10, the bone fastener's 58 orientation may be changed by rotation, deflection, or both.

The bone fastener 58 has a fastener head 10 and a bone engagement feature 64. The fastener head 10 has a surface that contacts a surface on the capture ring 42. In the embodiment illustrated in the figures the distal surface 12 of the head 10 is complementary to the internal contours 44 of the capture ring 42, both of which are frusto-spherical. The fastener head 10 may include a driver engagement feature 14, similar to the driver engagement feature 76 that may be found on the locking element 68. The driver engagement feature 14 functions to receive a driving tool, such as a screwdriver, to rotate or otherwise drive the fastener into the bone. In the embodiment illustrated in FIG. 4 the fastener engagement feature 64 in the fastener head 10 is a hexalobular internal feature, but any known fastener engagement feature 64 could be used (e.g., flathead, hex-head, and Phillips engagement features).

The bone engagement feature 64 secures the fastener 58 to the bone. An example of such a feature is a shank 4 comprising one or more screw-threads. The shank 4 may have a threaded point to facilitate attachment. The shank's 4 diameter is independent of the head's 10 diameter, which is made possible by the use of the narrow capture ring 42 to retain the head 10. Some embodiments of the shank 4 have a diameter that exceeds that of the head 10. In other embodiments the diameter of the shank 4 is equal to or less than that of the head 10.

The bone anchor 2 may be constructed of any suitable materials, including biocompatible materials. Some embodiments of the bone anchor 2 are constructed of non-absorbable biocompatible materials. Specific examples of such suitable materials include titanium, alloys of titanium, steel, and stainless steel. Parts of the bone anchor 2 could conceivably be made from non-metallic biocompatible materials, which include aluminum oxide, calcium oxide, calcium phosphate, hydroxyapatite, zirconium oxide, and polymers such as polypropylene.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

The following is claimed:

1. A bone anchor for securing a rod to a bone, the anchor comprising:
   a rod housing including a base, a pair of upright arms extending from the base to an upper proximal end, and a longitudinal axis extending though a distal opening in the base and a proximal opening in the upper proximal end, the pair of upright arms separated by a rod channel, and the base including an internal groove;
   a capture ring situated within the groove, the capture ring having a capture surface; and
   a bone fastener extending through the distal opening in the rod housing and including a fastener head and a shank having a bone engagement feature, the head situated within the base and having a surface that mates with the capture surface of the capture ring to maintain a connection between the bone fastener and the rod housing, wherein the capture ring is oriented at an angle oblique to a longitudinal axis of the fastener head when the fastener head is at maximum angulation relative to the longitudinal axis of the rod housing, the longitudinal axis of the fastener head extending from a distal end to a proximal end thereof.

2. The bone anchor of claim 1, wherein the capture ring comprises a slit that is narrower than the fastener shank, such that the slit allows the capture ring to be transiently compressed.

3. The bone anchor of claim 1, wherein the capture ring comprises exactly one slit that is narrower than the fastener shank, such that the slit allows the capture ring to be transiently compressed.

4. The bone anchor of claim 1, wherein the capture ring comprises an external surface that is frusto-spherical.

5. The bone anchor of claim 1, wherein the capture ring comprises an internal surface that is frusto-spherical.

6. The bone anchor of claim 5, wherein the capture ring comprises an external surface that is frusto-spherical.

7. The bone anchor of claim 1, comprising a load ring positioned within the base distal to the rod channel and proximal to the capture ring, wherein the load ring is positioned to exert compressing force on the fastener head with a distal vector when the load ring receives compressing force from the rod with a distal vector.

8. The bone anchor of claim 1, wherein the base includes a distal internal wall at its distal end, and wherein said distal internal wall comprises a scalloped recess at an angle oblique to the longitudinal axis of the rod housing.

9. The bone anchor of claim 1, wherein the distal opening of the base has a minimum diameter that is larger than a maximum diameter of the fastener head.

10. The bone anchor of claim 1, wherein the bone fastener comprises a neck positioned between the fastener head and the shank, the neck having a diameter smaller than the diameter of the fastener shank.

11. The bone anchor of claim 1, wherein the bone fastener is a bone screw, and wherein the bone engagement feature is a screw thread.

12. The bone anchor of claim 1, wherein the shank has a maximum diameter that is greater than the diameter of the distal opening of the base.

13. The bone anchor of claim 1, wherein the capture ring articulates freely within the internal groove and the bone fastener head has a spherical surface that mates and articulates with the capture ring internal surface.

14. The bone anchor of claim 1, wherein the bone fastener head has a spherical surface that is complementary to an internal surface of the capture ring, and wherein the bone fastener head articulates relative to the capture ring so as to form a universal joint.

15. The bone anchor of claim 1, wherein the rod channel is approximately perpendicular to the longitudinal axis of the rod housing.

16. The bone anchor of claim 1, wherein the rod channel is dimensioned to accommodate the rod.

17. The bone anchor of claim 1, wherein the upper distal end of the upright arms comprises an internal locking element engagement feature.

18. The bone anchor of claim 1, wherein the capture ring has a diameter that is smaller than the diameter of the bone fastener head.

19. The bone anchor of claim 1, wherein the upper distal end of the upright arms comprise an external guide assembly engagement feature.

20. A bone anchor for securing a rod to a bone, the anchor comprising:
- a rod housing including a base, a pair of upright arms extending from the base to an upper proximal end, a distal opening in the base, and a proximal opening in the upper proximal end, the pair of upright arms separated by a rod channel, and the base including an internal groove;
- a capture ring situated within the groove, the capture ring having a capture surface; and
- a bone fastener extending through the distal opening in the rod housing and including a fastener head and a shank having a bone engagement feature, the head situated within the base and having a surface that mates with the capture surface of the capture ring to maintain a connection between the bone fastener and the rod housing, wherein the capture ring is oriented at an angle oblique to a longitudinal axis of the fastener head when the fastener head is at minimum angulation relative to the longitudinal axis of the rod housing, the longitudinal axis of the fastener head extending from a distal end to a proximal end thereof.

* * * * *